United States Patent [19]

Uhing

[11] Patent Number: 4,758,684
[45] Date of Patent: Jul. 19, 1988

[54] REACTION PRODUCTS OF POLYCYCLIC OLEFINS WITH $P_4S_{10}$ AND $PSX_3$

[75] Inventor: Eugene H. Uhing, Omaha, Nebr.

[73] Assignee: Akzo America Inc., New York, N.Y.

[21] Appl. No.: 829,369

[22] Filed: Feb. 13, 1986

[51] Int. Cl.$^4$ .............................................. C07F 9/00
[52] U.S. Cl. .................................................... 558/82
[58] Field of Search ........................................ 558/82

[56] References Cited

U.S. PATENT DOCUMENTS 4,540,526  9/1985  Uhing ................................... 558/82

Primary Examiner—Anton H. Sutto
Attorney, Agent, or Firm—Richard P. Fennelly; Louis A. Morris; Francis W. Young

[57] ABSTRACT

Polycyclic olefins such as camphene, norbornene and bicycloheptadiene among others are reacted with $P_4S_{10}$ and $PSX_3$, wherein X is selected from the group consisting of chlorine and bromine, at a temperature from about 50° C. to about 250° C. The process can be run at atmospheric pressure. Further, the resulting halides can be further reacted with alcohols, mercaptans and amines to form other novel derivatives. The reaction products obtained can be used in lubricating oil compositions.

11 Claims, No Drawings

REACTION PRODUCTS OF POLYCYCLIC OLEFINS WITH P₄S₁₀ AND PSX₃

BACKGROUND OF THE INVENTION

1. Field of the Invention

The present invention relates to new compounds which can be characterized as reaction products of polycyclic olefins with $P_4S_{10}$ and $PSX_3$, wherein X is Cl or Br.

2. Related Art

Reactions of an alkyl halide or an aryl halide with $P_4S_{10}$ and $PCl_3$ are described in U.S. Pat. No. Re. 30,279, May 20, 1980, to Toy et al. The reactions are conducted in an autoclave at elevated temperature to produce alkyl phosphorus halides.

U.S. Pat. No. 3,988,368 (Ura et al., Oct. 26, 1976) discloses a process for preparing phenylphosphonothioic dichloride. In this process benzene is reacted with $PSCl_3$ in the presence of a catalyst. These catalysts include $P_2S_5$ and $PCl_3$ or $AlCl_3$ and $P_2S_5$.

U.S. Pat. No. 4,231,970 (Uhing, Nov. 4, 1980) discloses certain reaction products of unsaturated hydrocarbons with $P_4S_{10}$ and $PSX_3$ wherein X is chlorine or bromine. These reactions are carried out under autogenous pressure.

U.S. Pat. No. 3,726,918 (Toy et al., Apr. 10, 1973) discloses the preparation of alkyl or aryl phosphonothioic dihalides by the reaction of an alkyl halide or an aryl halide with a pentavalent thiophosphorus compound having at least two halogens attached thereto and preferably three halogens such as thiophosphorylhalide, in the presence of an halogen acceptor, such as phosphorus or sulfur, under at least autogenous pressure at a temperature of from 200° C. to 450° C.

U.S. Pat. No. 4,540,526 (Uhing, Sept. 10, 1985) discloses reaction products of unsaturated hydrocarbons with $P_4S_{10}$ and $PSX_3$ wherein X is chlorine or bromine. The reaction proceeds under autogenous pressure at temperatures from about 90° C. to about 250° C.

The reactions of polycyclic olefins with $P_4S_{10}$ and $PSX_3$ and other compositions and methods described in the present invention are not disclosed in the prior art.

SUMMARY OF THE INVENTION

In accordance with the present invention, novel polycyclic dithiophosphonyl halides which comprise the products of the reaction of a polycyclic olefin $P_4S_{10}$ and $PSX_3$, wherein X is selected from the group consisting of Cl and Br, at a temperature from about 50° C. to about 250° C. are disclosed. Further, novel compositions selected from the group consisting of

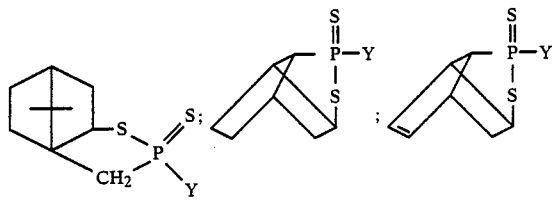

and isomers thereof; wherein Y is selected from the group consisting of: halogens; —OR; —SR; and —NRR¹ wherein R and R¹ are selected independently in each occurrence above from the group consisting of hydrogen, hydrocarbyl and hetero-substituted hydrocarbyl wherein the hetero-atom is selected from the group consisting of O and S are disclosed.

This invention further discloses methods of making these novel compositions and related compositions and further discloses lubricating oil compositions which comprises a lubricating base stock and at least one of the novel compositions.

DETAILED DESCRIPTION OF THE INVENTION

The present invention discloses novel compounds, novel processes for making these and related compounds, and novel compositions including the novel compounds as constituents.

The novel compositions of this invention can be classified into two broad groups, one being polycyclic dithiophosphonyl halides and the other being halide derivatives of these halides wherein the halide groups are substituted for by other groups. Exemplary polycyclic olefins and the corresponding novel reaction products, both halides and their derivatives, of the present invention include, but are not limited to the following:

| Polycyclic Olefins | Halides | Other Derivatives |
|---|---|---|
| 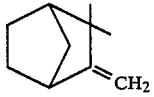 (camphene) | 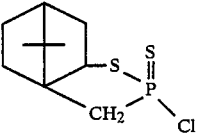 | 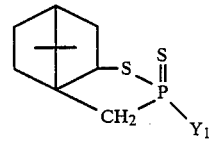 |

$Y_1 = $ —OH, —SCH₃, 

| Polycyclic Olefins | Halides | Other Derivatives |
|---|---|---|
| (alpha-pinene) | | |
| (beta-pinene) | | |
| (norbornene) | | |
| (bicycloheptadiene) | | |

The first group of novel compounds disclosed by this invention are polycyclic dithiophosphonyl halides. These compounds comprise the products of the reaction of a polycyclic olefin, $P_4S_{10}$ and $PSX_3$ wherein X is selected from the group consisting of chlorine and bromine, at a temperature from about 50° C. to about 250° C. Typical polycyclic olefins are selected from the group consisting of camphene, norbornene, bicycloheptadiene, alpha- and beta-pinene. When camphene is the polycyclic olefin the yields of the final product are particularly good and, therefore, camphene is a preferred polycyclic olefin.

The other group of novel compounds disclosed by this invention are derivatives of the above halides wherein the halide groups are replaced by other groups. These compositions are selected from the group consisting of:

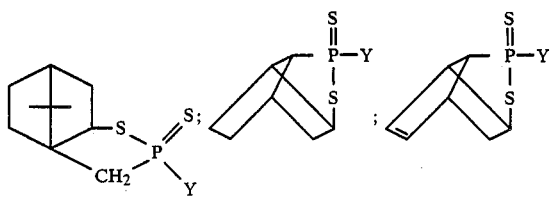

and isomers thereof; wherein Y is selected from the group consisting of halogen; —OR; —SR; and —NRR$^1$ wherein R and R$^1$ are selected independently in each occurrence above from the group consisting of hydrogen, hydrocarbyl and hetero-substituted hydrocarbyl, wherein the hetero-atom is selected from the group consisting of oxygen and sulfur. When Y is halogen, these compounds are the same as those disclosed above in the first group of novel compounds.

The process of the present invention for preparing polycyclic dithiophosphonyl halides comprises reacting a polycyclic olefin, $P_4S_{10}$ and $PSX_3$, wherein X is selected from the group consisting of Cl and Br, at a temperature from about 50° C. to about 250° C.

The resulting polycyclic dithiophosphonyl halides can be further reacted with a compound selected from the group consisting of an alcohol and an alkoxide of the respective formulae ROH and ROM, wherein R is hydrocarbyl and M is an alkali metal, in the presence of an acid acceptor except when the alkoxide is used. An acid acceptor can be used with the alkoxide, however the acid acceptor is not a necessary component in that case and when one is used, e.g. pyridine, it functions only as a solvent. This process yields novel polycyclic dithiophosphonyl derivatives in which the halide is replaced with a —OR group. R can be selected from the group consisting of hydrogen and hydrocarbyl. Preferred choices for R can be selected from the group consisting of hydrogen, $C_1$–$C_{18}$ alkyl, $C_6$–$C_{10}$ aryl and $C_6$–$C_{18}$ alkylaryl. The acid acceptor can be a tertiary amine, for example pyridine and triethylamine. The primary or secondary amine can react with the halides to form compounds disclosed below. Sodium is a preferred alkali metal.

The process of this invention also includes the reaction of the polycyclic dithiophosphonyl halides with compounds selected from the group consisting of HSR and MSR, wherein R is hydrocarbyl and M is an alkali metal, in the presence of an acid acceptor except when MSR is used. The products of this process are novel derivatives having a —SR group substituted for the halide group. R and the acid acceptor are defined above.

A further process of this invention includes the reaction of the polycyclic dithiophosphonyl halide with a compound of formula HNRR$^1$ wherein R and R$^1$ are selected independently from the group consisting of hydrogen, hydrocarbyl and hetero-substituted hydrocarbyl, wherein the hetero-atom is selected from the group consisting of O and S. The products of this process are novel derivatives of the polycyclic dithiophosphonyl halide wherein the halide is replaced with a —NRR[1] group.

Another process of this invention for making dithiophosphonyl halide comprises reacting an olefin having a hetero-atom such as sulfur, e.g. allyl methyl sulfide, with $P_4S_{10}$ and $PSX_3$ wherein X is selected from the group consisting of Cl and Br, at a temperature from about 50° C. to about 250° C. at atmospheric pressure.

The reactants utilized in the process of the present invention are generally employed in stoichiometric amounts, although an excess of any reactant can be used if desired. The quantity of undesired side-products, however, is minimized by the use of approximately stoichiometric amounts of reactants. No catalyst is used or is necessary in the processes of the present invention.

The processes are carried out at elevated temperature. The reaction temperatures range from about 50° C. to about 250° C.

The processes of this invention can all be run at atmospheric or at elevated pressures, e.g., autogenous. Atmospheric pressure is preferred for the processes using the high-boiling polycyclic olefins disclosed in this invention. In other preparations of dithiophosphonyl halides disclosed in the prior art, the use of pressure is an essential limitation. The processes of this invention offer greater flexibility and allow the convenience of running at atmospheric pressure.

The reaction times can vary over relatively wide ranges and can easily be determined by one of ordinary skill in the art. Factors affecting reaction time can include the choice of a specific reactant and temperature. Increases in temperature and reactant concentration result in decreased reaction times. Dilute reactants require longer reaction times than concentrated reactants. Typical reaction times are from about 1 to about 24 hours.

The products of these reactions can be purified by vacuum distillation and other conventional methods such as, e.g. extraction, sublimation and crystallization.

The identification of the resulting products can be achieved by infrared spectra, $^1H$ nuclear magnetic resonance spectra, $^{31}P$ nuclear magnetic resonance spectra, boiling point analysis and elemental analysis.

This invention further discloses lubricating oil compositions. These compositions comprise a lubricating base stock and at least one of the novel polycyclic dithiophosphonyl halides disclosed above. Further lubricating oil compositions comprises lubricating base stock and at least one of the novel derivatives of polycyclic dithiophosphonyl halides described above.

The novel compounds disclosed above are useful by themselves or as intermediates to prepare agricultural chemicals, e.g. insecticides, herbicides and miticides; lubricants and polymer additives. For example,

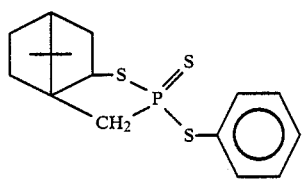

was found to be miticidally-active on the two spotted mites. As another example,

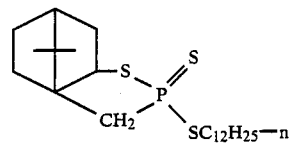

was found to be active as an anti-wear oil additive. Four ball wear results (ASTM D2266) indicate that this product imparts good anti-wear protection in a parafinic base oil. The anti-wear protection obtained was better than that of a commercial zinc dialkylphosphorodithioate (ELCO 108, a product of The Elco Corporation) when both were used at 1 weight percent concentration in SUNPAR 120, a parafinic base oil product of Sun Oil Company. The test conditions were 1800 rpm at 40 kg load and 54° C.

|  | Wear Scar mm |
| --- | --- |
| SUNPAR 120 | 1.98 |
| SUNPAR plus novel compound | 0.46 |
| SUNPAR plus ELCO 108 | 0.62 |

The following experiments describe various embodiments of this invention. Other embodiments will be apparent to one of ordinary skill in the art from a consideration of this specification or practice of the invention disclosed herein. It is intended that the specification and experiments be considered as exemplary only, with the true scope and spirit of the invention being indicated by the claims which follow the experiments.

EXPERIMENT 1

Preparation of

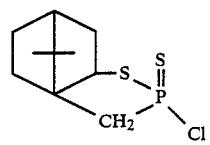

MW=266.8.

In a 300 ml round-bottom pyrex reaction flask were placed 30.6 g camphene (0.2246 moles, MW=136.24, 95% assay), 12.71 g $PSCl_3$ (0.075 moles, MW=169.40) and 16.7 g $P_4S_{10}$ (0.0376 moles, MW=444.54). The reaction flask was heated slowly to 125° C. with magnetic bar stirring used under an atmosphere of nitrogen. At about this temperature an exothermic reaction occurs which can require cooling to prevent the temperature from rising above 135° C. before all the $P_4S_{10}$ has reacted.

The temperature of the reactants were raised from 125° C. to 175° C. over a 4 hour period. The reaction temperature is kept at 175° C.-200° C. for 4 hours. Some HCl was liberated at the high reaction temperature (0.04 moles). The reactants were then distilled under high vacuum to yield 29.1 g of crude product (48.6 weight percent theoretical yield), $bp_{0.05}$=120° C.-180° C., which crystallized on standing. This crude product was washed with 50 ml cold (0° C.) heptane to yield 14.5 g of product (mp 104° C.-106° C.) which was recrystallized by dissolving in 300 ml hot (75° C.) heptane then cooled to room temperature to yield 13.6 g, mp 108.9° C. product. Analysis found: 13.4 Cl; 12.1 P; 24.1 S. This was calculated for C₁₀H₁₆ ClPS₂ (MW=266.8); 13.3 Cl; 11.6 P; 24.0 S. The structure is based on known isomerization of camphene and $^1$H, $^{13}$C, $^{31}$P-NMR analyses of the product.

EXPERIMENT 2

Preparation of

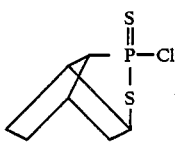

MW=224.7

In a 100 ml round-bottom distillation flask were placed 14.1 g norbornene (0.15 moles, MW=94.16), 8.5 g PSCl₃ (0.05 moles, MW=196.4) and 11.1 g P₄S₁₀ (0.025 moles, MW=444.54). The flask was equipped with a reflux condenser and magnetic stirring bar. While keeping the reactants under an atmosphere of nitrogen, the reaction mixture was heated to reflux with an oil bath at 105° C. After 4½ hours of heating, the oil bath temperature was raised to 145° C. bringing the internal liquid temperature to 122° C. The heating source was then changed to a heating mantle and the reaction temperature slowly raised to 215° C. over a 13 hour period. The resulting crude product was then distilled under high vacuum bp$_{0.01}$=120° C.-150° C. The distilled product crystallized on standing. The yield was 14.0 g or 42 weight percent of the theoretical yield. The crystalline product was dissolved in 100 ml hot heptane and allowed to cool to room temperature. The yield of recrystallized material was 6.4 g. Analysis found: 15.7 Cl; 14.0 P; 28.8 S. This calculated for C₇H₁₀ClPS₂ (MW=224.7), 15.8 Cl; 13.8 P; 28.5 S. Analysis by $^{31}$P-NMR revealed that the product contained two closely related isomers and a small amount of a third component. Analysis by GC mass spectroscopy indicated that these isomers all have the same molecular weight. The structure shown is one of several possible isomers.

EXPERIMENT 3

Preparation of

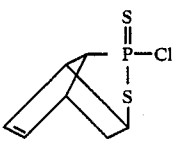

MW=222.69.

In a 250 ml round-bottom distillation flask were placed 27.6 g of bicyclo[2.2.1]hepta-2,5 diene (0.3 moles, MW=92.14), 25.4 g PSCl₃ (0.15 mole, MW=169.4, or 0.05 molar excess). The distillation flask was fitted with a reflux condenser and a magnetic bar for stirring. While keeping the reactants under nitrogen atmosphere, they were heated to 85° C. at which point heat was liberated and the heating mantle was removed. After allowing the reactants to react at 85° C.-95° C., the reaction mixture was heated slowly to 180° C. over a 4 hour period. At this point, 10 ml of PSCl₃ was added and the reaction mixture held at 150° C.-180° C. for 18 minutes. The product was then distilled bp$_{0.1}$=150° C.-180° C. after removing low boilers at 10-15 mm Hg. The distillation yielded 18.8 g which formed some crystals on standing. The crude product was dissolved in 100 ml heptane at 25° C. and cooled to 0° C. 10.6 g of crystals were isolated with a melting point of 72° C.-73° C. Mass spectra analysis showed the compound to have molecular weight of 222 with 1 Cl. The expected molecular weight was 222.69. The structure of the product is based on $^1$H, $^{13}$C and $^{31}$P-NMR analyses.

EXPERIMENT 4

Preparation of

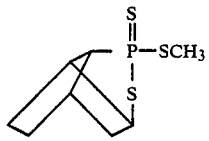

In a 50 ml reaction flask were placed 7 ml of 25 weight percent CH₃ONa in methanol (0.03 moles CH₃ONa). Into this solution was bubbled 1.44 g of CH₃SH (0.03 moles, MW=48.1). The methanol is removed under vacuum to leave CH₃SNa. 30 ml of pyridine as a solvent and 6.72 g

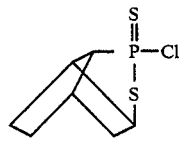

(0.03 moles, MW=224) were added. This reaction mixture was heated to 95° C.-100° C. for 1 hour. Then the reaction mixture was evaporated to dryness under vacuum and 50 ml of toluene was added and refluxed for 1 hour. After evaporating the toluene, the sample was placed in CH₂Cl₂ (50 ml) and washed with water to remove sodium chloride. The yield after removing the CH₂Cl₂ solvent was 5.2 g (theoretical yield expected for 0.03 moles of product is 7.8 g of MW=236). The product was a thick syrup.

EXPERIMENT 5

Preparation of

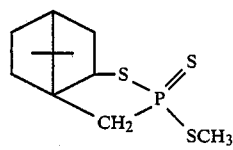

Using a similar procedure as described in Experiment 4, 7.98 g of

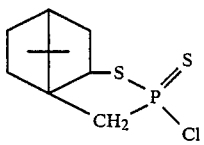

(0.03 moles, MW=266) was added to the CH₃SNa. After heating at 100° C. for 2 hours, the pyridine was removed under vacuum. The crude product was slurried in 50 ml of CH₂Cl₂ and washed with 50 ml water to remove sodium chloride. The CH₂Cl₂ was removed under vacuum to yield 7.7 g (theoretical yield expected 8.3 g, MW=278) of a yellow product which crystallized on standing (mp=71° C.-76° C.). Analysis by ³¹P-NMR indicated that the product had a purity of 96% with delta=115 ppm. Mass spectra analysis confirmed the product's molecular weight.

EXPERIMENT 6

Preparation of

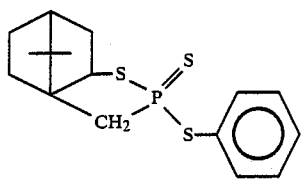

The basic procedure described in Experiment 4 was used except that 3.3 g thiophenol

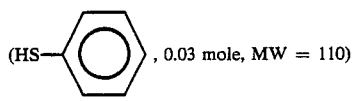

was added to the CH₃ONa to make

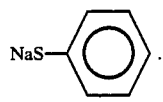

After refluxing the pyridine solvent for 2 hours, it was distilled off under vacuum. Then 50 ml of CH₂Cl₂ and 50 ml of water were added. After stirring, the layers were separated and the CH₂Cl₂ layer was evaporated. A crystalline product, mp 98° C.-104° C., weighing 9.1 g was isolated (theoretical yield is 10.2 g for a product of MW=340). Analysis by ³¹P-NMR showed the product to be 91% pure having a delta=116 ppm. Mass spectra analysis confirmed the products molecular weight.

EXPERIMENT 7

Preparation of

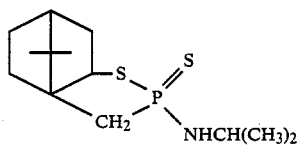

In a 100 ml three-neck reaction flask equipped with a magnetic stirring bar, a reflux condenser and a dropping funnel were placed 7.98 g

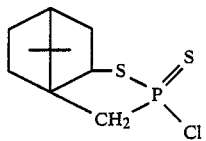

(0.03 moles, MW=266) and 30 ml of pyridine. 3.2 ml of NH₂CH(CH₃)₂ (Sp.Gr. 0.69, 2.21 g, 0.037 moles, MW=59.11) was placed in the dropping funnel and added dropwise to the reaction mixture. The reaction mixture was heated at 100° C. for 15 minutes. The solvent is distilled off under vacuum. 50 ml of CH₂Cl₂ and 50 ml of 1N aqueous HCl were added. The organic layer was separated and extracted with 50 ml of 1N sodium hydroxide. Again the layers were separated and the organic layer was stripped under vacuum. A white solid was obtained, mp 65° C.-70° C. weighing 8.2 g (theoretical yield is 8.67 g for a product having MW=289). Analysis by ³¹P-NMR showed a product purity of 80%. Mass spectra analysis confirmed the product's molecular weight.

EXPERIMENT 8

Preparation of

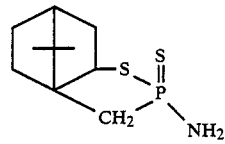

In a 50 ml three-neck reaction flask equipped with a gas inlet tube, a reflux condenser and a magnetic stirring bar were placed 7.98 g

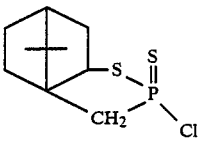

(0.03 moles, MW=266) and 35 ml of tetrahydrofuran as the solvent. Anhydrous ammonia gas was then bubbled into the reaction mixture. The reactants were heated to reflux for 2 hours with ammonia gas addition. The solvent was removed under vacuum and the solid residue was washed with 50 ml of water. The water insoluble product is removed by filtration. The yield was 7.4 g, mp=101° C.-105° C. (theoretical yield is 7.41 g for a product of MW=247). Mass spectra and ³¹P-NMR analyses confirmed the products formation.

EXPERIMENT 9

Preparation of

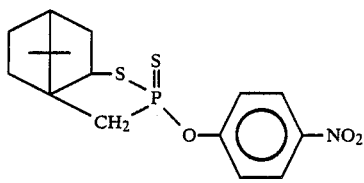

The procedure described in Experiment 6 was used except that 4.2 g of para-nitrophenol (0.3 mole, MW=139) was converted to the sodium salt. The reactants were heated and refluxed for 2 hours. The solvent was stripped off and 25 ml of CH$_2$Cl$_2$ and 25 ml of 1N sodium hydroxide were added. After repeating the 1N sodium hydroxide washing, the organic layer was washed with 1N HCl. The organic layer was then evaporated under vacuum to yield 10.0 g of a solid having mp=94° C.–101° C. The expected yield is 11 g for a compound having MW=369.

EXPERIMENT NO. 10

Preparation of

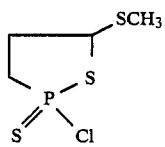

MW=218.69

In a 250 ml three-neck reaction flask equipped with a magnetic stirring bar, reflux condenser, thermometer and kept under an atmosphere of N$_2$ were placed 72 g allylmethyl sulfide (0.816 mole, MW=88.17), 46 g PSCl$_3$ (0.272 mole, MW=169.4) and 60.4 g P$_4$S$_{10}$ (0.136 mole, MW=444.5). The reaction mixture was heated slowly to 85° C. at which temperature a slightly exothermic reaction took place. At a reaction temperature of 90° C., all the P$_4$S$_{10}$ was reacted. The reaction mixture was heated at 130° C. for 2 hours, then at 140° C. for 15 minutes. At this point, HCl was liberated and the reaction was stopped. The reaction mixture was distilled, bp$_{0.03}$ at 100° C.–160° C. The distillation yielded 81.8 g or 56 weight percent of the theoretical yield. The product was again distilled to yield a constant boiling fraction bp$_{0.05}$, 139° C. N$_D^{25}$=1.6645. Analysis found: 16.2 Cl; 14.0 P; 44.5 S, calculated for C$_4$H$_8$ClPS$_3$ 16.2 Cl; 14.2 P; 44.05. The product was a yellow oil. The structure was based on NMR analyses.

What is claimed is:

1. Polycyclic dithiophosphonyl halides which comprise the products of the reaction of a polycyclic olefin, P$_4$S$_{10}$, and PSX$_3$ wherein X is selected from the group consisting of Cl and Br, at a temperature from about 50° C. to about 250° C.

2. A composition selected from the group consisting of:

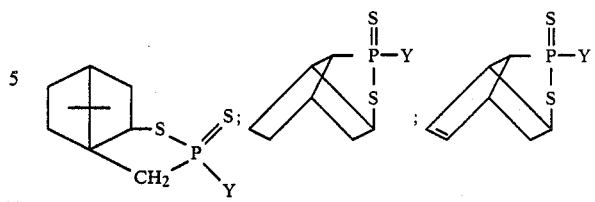

and isomers thereof; wherein Y is selected from the group consisting of: halogens; —OR; —SR; and —NRR$^1$ wherein R and R$^1$ are selected independently in each occurrence above from the group consisting of hydrogen, hydrocarbyl and hetero-substituted hydrocarbyl wherein the hetero-atom is selected from the group consisting of O and S.

3. The composition of claim 2 of the formula:

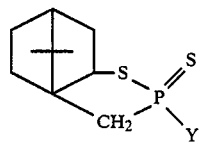

wherein Y is selected from the group consisting of Cl and Br.

4. The composition of claim 2 of the formula:

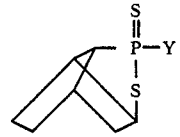

wherein Y is selected from the group consisting of Cl and Br.

5. The composition of claim 2 of the formula:

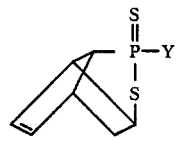

wherein Y is selected from the group consisting of Cl and Br.

6. The composition of claim 2 of the formula:

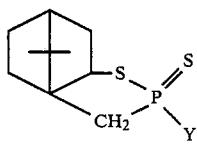

wherein Y is selected from the group consisting of: —OR; —SR; and —NRR$^1$.

7. The composition of claim 2 of the formula:

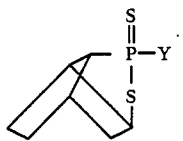

wherein Y is selected from the group consisting of:

—OR; —SR; and —NRR[1].

8. The composition of claim 2 of the formula:

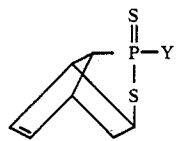

wherein Y is selected from the group consisting of: —OR; —SR; and —NRR[1].

9. A process for preparing polycyclic dithiophosphonyl halides comprising reacting a polycyclic olefin, $P_4S_{10}$, and $PSX_3$ wherein X is selected from the group consisting of Cl and Br, at a temperature from about 50° C. to about 250° C.

10. The process of claim 9 wherein the polycyclic olefin is selected from the group consisting of camphene, norbornene, bicycloheptadiene, and alpha and beta pinene.

11. The process of claim 9 wherein the polycyclic olefin is camphene.

* * * * *